US011266813B2

(12) United States Patent
Harders et al.

(10) Patent No.: US 11,266,813 B2
(45) Date of Patent: *Mar. 8, 2022

(54) INTERLOCKING LOW PROFILE GRIPPING DEVICE

(71) Applicant: BioDerm, Inc., Largo, FL (US)

(72) Inventors: James Alan Harders, Indian Rocks Beach, FL (US); Shawn Stone, St. Petersburg Beach, FL (US)

(73) Assignee: BioDerm, Inc., Largo, FL (US)

(*) Notice: Subject to any disclaimer, the term of this patent is extended or adjusted under 35 U.S.C. 154(b) by 279 days.

This patent is subject to a terminal disclaimer.

(21) Appl. No.: 16/454,806

(22) Filed: Jun. 27, 2019

(65) Prior Publication Data

US 2019/0314611 A1 Oct. 17, 2019

Related U.S. Application Data

(63) Continuation of application No. 15/658,254, filed on Jul. 24, 2017, now Pat. No. 10,369,332.
(Continued)

(51) Int. Cl.
A61M 25/02 (2006.01)
(52) U.S. Cl.
CPC ....... A61M 25/02 (2013.01); A61M 2025/024 (2013.01); A61M 2025/028 (2013.01); A61M 2025/0266 (2013.01)
(58) Field of Classification Search
CPC ............ A61M 25/02; A61M 2025/026; A61M 2025/0266; A61M 2025/0206;
(Continued)

(56) References Cited

U.S. PATENT DOCUMENTS 3,302,913 A 2/1967 Collyer et al.
3,834,380 A 9/1974 Boyd
(Continued)

FOREIGN PATENT DOCUMENTS

WO WO2005104776 11/2005
WO WO2007028007 3/2007
(Continued)

OTHER PUBLICATIONS

United States Patent and Trademark Office, Office Action for U.S. Appl. No. 12/620,844, dated Feb. 16, 2012.
(Continued)

Primary Examiner — Emily L Schmidt
(74) Attorney, Agent, or Firm — Hill Ward Henderson, P.A.; Stephen E. Kelly

(57) ABSTRACT

A low profile gripping device having a locking assembly attached to a base having a table, wherein the locking assembly comprises a locking strap with pairs of fins disposed for insertion into an aperture of a buckle. The locking assembly comprises an offset anchor block having opposing sides, the locking strap attached to one side, and the buckle attached to the opposing side. The interface between the locking strap and the anchor block forms a creased groove for seating a flexible polymer tube or polymer coated cable. The creased groove is located above the table such that the seated tube or cable is substantially centered above the base. The locking strap is inserted through the aperture to secure the tube or cable in the creased groove, and the fins retain the locking strap in fixed relation to the buckle.

20 Claims, 7 Drawing Sheets

Related U.S. Application Data

(60) Provisional application No. 62/483,719, filed on Apr. 10, 2017.

(58) Field of Classification Search
CPC ........ A61M 2025/0253; A61M 5/1418; A61M 2025/0273
See application file for complete search history.

(56) References Cited

U.S. PATENT DOCUMENTS

| | | | |
|---|---|---|---|
| 4,316,461 A | 2/1982 | Marais et al. | |
| 4,416,664 A | 11/1983 | Womack | |
| 4,563,177 A | 1/1986 | Kamen | |
| 4,662,873 A * | 5/1987 | Lash | A61M 25/02 128/DIG. 26 |
| 4,838,878 A | 6/1989 | Kalt et al. | |
| 4,915,694 A | 4/1990 | Yamamoto et al. | |
| 4,932,943 A | 6/1990 | Nowak | |
| 4,981,475 A | 1/1991 | Haindl | |
| 5,073,170 A | 12/1991 | Schneider | |
| 5,084,026 A | 1/1992 | Shapiro | |
| 5,147,320 A | 9/1992 | Reynolds et al. | |
| 5,167,630 A | 12/1992 | Paul | |
| 5,195,981 A | 3/1993 | Johnson | |
| 5,207,652 A | 5/1993 | Kay | |
| 5,232,453 A | 8/1993 | Plass et al. | |
| 5,235,729 A * | 8/1993 | Tiegs | F16B 2/08 24/20 CW |
| 5,266,401 A | 11/1993 | Tollini | |
| 5,300,037 A | 4/1994 | Delk et al. | |
| 5,304,146 A | 4/1994 | Johnson et al. | |
| 5,496,283 A | 3/1996 | Alexander | |
| 5,643,217 A | 7/1997 | Dobkin | |
| 5,681,290 A | 10/1997 | Alexander | |
| 5,685,859 A | 11/1997 | Kornerup | |
| 5,755,225 A | 5/1998 | Hutson | |
| 5,797,884 A | 8/1998 | Byrd | |
| 5,897,519 A | 4/1999 | Shesol et al. | |
| 6,102,347 A | 8/2000 | Benoit | |
| 6,361,523 B1 | 3/2002 | Bierman | |
| 6,572,588 B1 * | 6/2003 | Bierman | A61M 25/02 128/DIG. 26 |
| 6,689,105 B2 | 2/2004 | Tollini | |
| 7,413,561 B2 | 8/2008 | Raulerson et al. | |
| 7,722,571 B2 | 5/2010 | Bierman et al. | |
| 2004/0034330 A1 | 2/2004 | Bierman et al. | |
| 2005/0038453 A1 | 2/2005 | Raulerson | |
| 2005/0070852 A1 | 3/2005 | Wright | |
| 2006/0041233 A1 | 2/2006 | Bowen | |
| 2006/0276752 A1 | 12/2006 | Bierman et al. | |
| 2007/0142784 A1 | 6/2007 | Dikeman et al. | |
| 2008/0249476 A1 * | 10/2008 | Bierman | A61M 25/01 604/175 |
| 2009/0139061 A1 | 6/2009 | Nishtasia | |
| 2009/0216197 A1 | 8/2009 | Russo | |
| 2009/0326474 A1 | 12/2009 | Bierman et al. | |
| 2010/0217201 A1 * | 8/2010 | Lee | A61M 25/02 604/177 |
| 2011/0118670 A1 | 5/2011 | Kay et al. | |
| 2012/0016312 A1 * | 1/2012 | Brown | A61M 25/02 604/180 |
| 2012/0203182 A1 * | 8/2012 | Kay | A61F 13/0269 604/180 |
| 2013/0165863 A1 * | 6/2013 | Nilson | A61M 25/02 604/180 |
| 2014/0046265 A1 | 2/2014 | Kay et al. | |
| 2014/0316339 A1 * | 10/2014 | Beran | A61M 25/02 604/180 |

FOREIGN PATENT DOCUMENTS

| | | |
|---|---|---|
| WO | WO2008090233 | 7/2008 |
| WO | WO2011060197 | 5/2011 |

OTHER PUBLICATIONS

United States Patent and Trademark Office, Office Action for U.S. Appl. No. 12/620,844, dated Sep. 17, 2012.
United States Patent and Trademark Office, Office Action for U.S. Appl. No. 13/136,669, dated Jul. 10, 2013.
United States Patent and Trademark Office, Office Action for U.S. Appl. No. 13/136,669, dated Apr. 15, 2014.
United States Patent and Trademark Office, Office Action for U.S. Appl. No. 14/024,963, dated Jul. 2, 2015.
United States Patent and Trademark Office, Office Action for U.S. Appl. No. 14/024,963, dated Feb. 3, 2016.
United States Patent and Trademark Office, Office Action for U.S. Appl. No. 15/420,592, dated Jul. 23. 2018.
International Searching Authority, International Search Report and Written Opinion for International Application No. PCT/US2010/055935, dated Mar. 28, 2011.
International Searching Authority, International Search Report and Written Opinion for International Application No. PCT/US2018/026909, dated Jul. 19, 2018.
United States Patent and Trademark Office, Office Action for U.S. Appl. No. 15/658,254, dated Jun. 25, 2018.
United States Patent and Trademark Office, Office Action for U.S. Appl. No. 15/658,254, dated Dec. 29, 2017.
International Bureau of WIPO, International Preliminary Report on Patentability for International Application No. PCT/US2018/026909, dated Oct. 24, 2019.
Extended European Search Report for International Application No. PCT/US2018/026909, dated Feb. 28, 2020.
United States Patent and Trademark Office, Office Action for U.S. Appl. No. 15/658,254, dated Aug. 28, 2017.

* cited by examiner

INTERLOCKING LOW PROFILE GRIPPING DEVICE

CROSS-REFERENCE TO RELATED APPLICATION

Pursuant to 35 U.S.C. § 120, this application is a continuation application of U.S. patent application Ser. No. 15/658,254, filed on Jul. 24, 2017, which pursuant to 35 U.S.C. §§ 119(e) claims the benefit of U.S. Provisional Patent Application Ser. No. 62/483,719, filed on Apr. 10, 2017, the entire contents of each of which are incorporated herein by this reference.

BACKGROUND

1. Field of Invention

The present gripping device relates to securement of catheters, and more particularly, to the securement of flexible polymer tubing and polymer coated cables.

2. Description of Related Art

The present catheter gripping device is particularly adapted for securing elongated members, such as flexible polymer tubing used in therapeutic treatments. These treatments may include medicinal fluid delivery or removal, human fluid delivery or removal, and other applications that require securing of polymer coated cables used with patient monitoring devices employed in a clinical, hospice, or home settings. These tubing or cable members may or may not be directly attached to a patient's body part or area, or on a fixture located near the patient.

There is a variety of polymer tubing used in clinical applications to provide treatments, as described above, through natural or created orifices or stomas. From time to time, the tubing must be secured to a patient's body in order for the delivery or supply system to travel with ambulatory patients and to non-ambulatory patients. These flexible polymer tubing members must be secured in a manner such that forces acting upon these flexible tubes or polymer coated cables do not cause dislodging of the tubes or cables during ambulatory action, involuntary action, or transportation of the patient. It can be stated that abrupt dislodging of these tubing members or cables may cause the therapy or monitoring activities to cease or possibly cause an injury to the patient. Additionally, there are several categories of electrical type cables (normally polymer coated) that are attached to patient monitors that can be mobile or stationary. These polymer coated cables must also be secured to a patient's person or to a fixture that is well placed so not as to induce any dangerous forces that may cause the cable to become dislodged from the patient or the device such as a patient oxygen monitor.

The flexible polymer tubing and or polymer coated cable outside diameter typically range in size from 3 French (1 millimeter ("mm")) to 47 French (15.67 mm), and all must be able to be secured to a patient's person or to a nearby fixture or other medical device. When the tubing and or cable is attached to a patient's person, it must be attached so that in the case of an ambulatory patient, the tubing and or cable cannot be snagged or entangled in such a manner that disrupts the therapy or monitoring activity. In most cases these tubes or cables are attached to an adhesive tape or patch, which is then attached to a patient's person by direct contact with patient's skin surface, namely, the epidermis of a patient. This placement onto the skin of a patient may offer some advantages of flexibility over a ridged fixture, such a bed rail or wheelchair device. Prior gripping devices use different securing modalities for attaching tubes or lines to a patient's person, such modalities including medical adhesive tape or patches made from a hydrocolloid substance.

However, notwithstanding this secondary securing modality, prior art for these flexible polymer tubing holders, also known as catheter securing devices, does not disclose features such as the mechanical design aspects which ensure the efficacy of the design to the application. As previously discussed, any unintentional movement by the flexible polymer tubing or polymer coated cable may cause a disruption of the therapy or monitoring activities and thus an adverse reaction could occur. Additionally, the previous art does not disclose how the securing devices will prevent damage, constriction, or other mechanical occlusion due to the bending of the flexible polymer tubing or polymer coated cable while attached to a patient's skin or person.

Therefore, what is needed is a low profile gripping device for securely retaining flexible polymer tubing or polymer coated cables, namely, by adhering the gripping device to a patient's skin.

SUMMARY OF THE PREFERRED EMBODIMENTS

The gripping device comprises one or more locking assemblies attached to a base, which is an elongate member having rounded ends and a central table surrounded by a sloping apron. The table is oriented in substantial alignment with a longitudinal axis of the base. The bottom of the base comprises one or more interface members to assist mechanical bonding of the base to a hydrocolloid patch.

Each locking assembly comprises an anchor block, a locking strap, and a buckle. The anchor block is secured to the base, and the anchor block has a first side and a second side separated by a crown. The first side of the anchor block has a recess for receiving the locking strap.

Each locking strap comprises a root, a spine, a tip, and a plurality of locking members, such as or fins, tabs, or the like. Each of the fins has a trailing edge oriented about perpendicular to the spine, and a leading edge oriented at about a 40° angle in relation to the trailing edge. The fins are disposed in pairs symmetrically about the spine. The pairs of fins are spaced at intervals along the spine such that the space between the pairs of fins defines a notch.

The root of the locking strap is anchored in the recess of the first side of the anchor block. The root comprises an elbow having a cutout groove on the inside of the elbow to promote flexibility. The interface between the elbow and the first side defines a creased groove for seating the tubing member to be secured by the gripping device.

Each buckle comprises a root and a distal end. The root is attached to the second side of the anchor block. The root comprises a yoke such that an aperture is defined by the second side of the anchor block and the yoke. To secure a tubing member, the tubing member is seated in the creased groove, and the locking strap is extended over the tubing member and inserted into the aperture until one or more pairs of fins passes through the aperture. Insertion of the locking strap continues until the locking strap snugly contacts the tubing member. The trailing edge of the fins that passed through the aperture then retain the locking strap in fixed relation to the buckle, thereby securing the tubing member in a manner snugly seated in the creased groove.

DETAILED DESCRIPTION OF THE PREFERRED EMBODIMENTS

Figure 1:
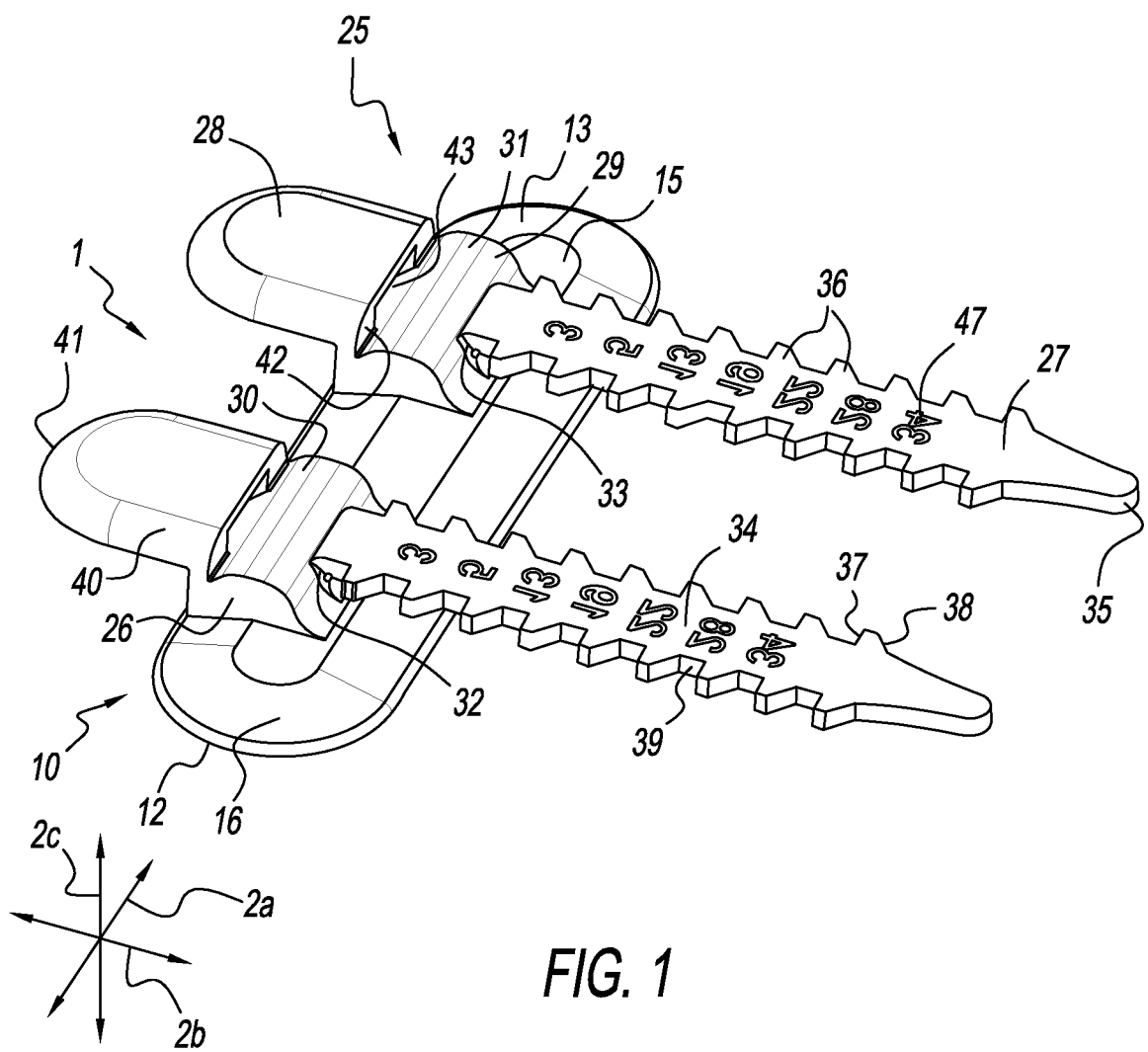
FIG. 1 is a perspective view of one embodiment of a gripping device in its undeformed shape.

With reference to the drawings, the gripping device will now be described with regard for the best mode and the preferred embodiments. In general, the device disclosed herein is a gripping device for securing polymer tubing and polymer coated cables to a medical patient's body. The embodiments disclosed herein are meant for illustration and not for limitation of the inventive scope. An ordinary practitioner will appreciate that it is possible to create many variations of the following embodiments without undue experimentation. To facilitate the following discussion, it is helpful to define a system for spatial reference. Referring to FIG. 1, the gripping device 1 is described in terms of a longitudinal direction 2a, a transverse direction 2b, and a vertical direction 2c.

One aspect of the present gripping device 1 is to secure flexible polymer tubing or flexible polymer coated cables, collectively referred to herein as "tubing members." These tubing members 5 are typically attached to medical equipment that provides direct therapy or monitoring of a patient, or introduces or removes fluids to or from the patient's body. The gripping device 1 is adapted for direct attachment to the surface of a patient's epidermis. This securement is accomplished by the assembly of the present catheter gripping device to a specially formulated hydrocolloid patch 11, which is manufactured in various sizes and shapes.

Referring to FIGS. 1-4, in one embodiment, the gripping device 1 comprises one or more locking assemblies 25 attached to a base 10. The base 10 is intended to secure the locking assemblies 25 to an adhesive patch 11, such as a hydrocolloid patch, which is adapted to removably attach to the skin of a medical patient. The base 10 is an elongate member with rounded ends 12, and the base 10 has a top 13 and a bottom 14 (See FIGS. 5 & 6). The top 13 of the base 10 has a central table 15 surrounded by a sloping apron 16. The table 15 is oriented in substantial alignment with a longitudinal axis 17 of the base 10. It is preferable, but not required, that the base 10 is substantially symmetric about its longitudinal axis 17.

Figure 5:
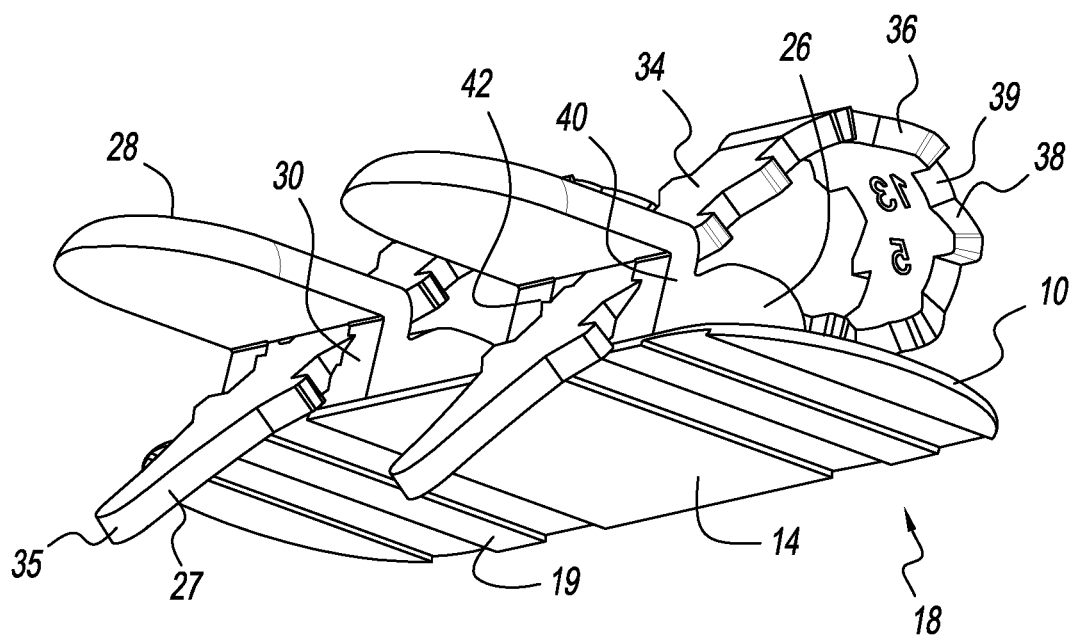
FIG. 5 is a bottom perspective view of one embodiment of a gripping device.
Figure 6:
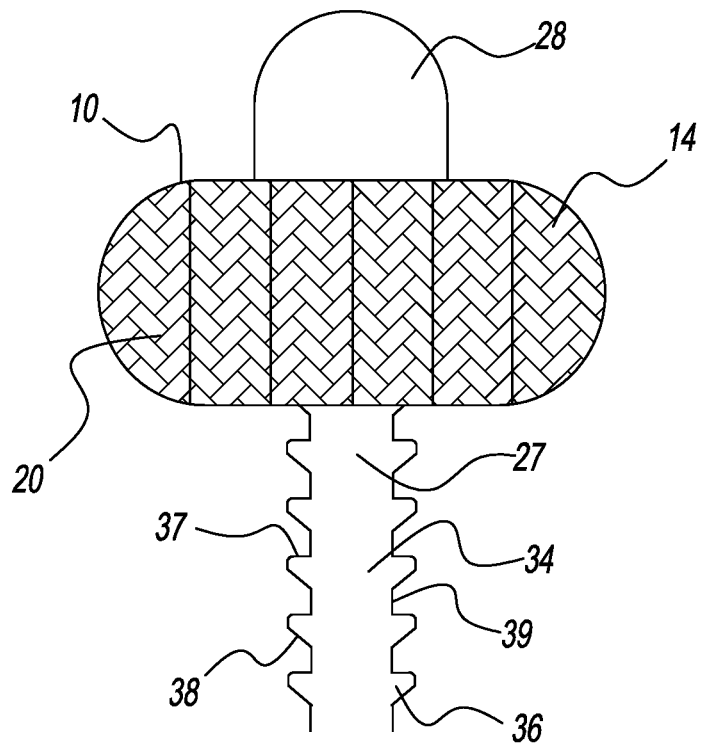
FIG. 6 is a bottom view of one embodiment of a gripping device.

In one embodiment, the base 10 is secured to the patch 11 by an adhesive. Referring to FIGS. 5 and 6, the bottom 14 of the base 10 comprises one or more interface members 18 to assist mechanical bonding between the base 10 and the adhesive. Examples of interface members 18 could be cleats 19 disposed in a dovetail orientation, a roughened surface 20, or some other equivalent interface feature capable of forming a mechanical bond with the cured adhesive disposed between the bottom 14 of the base 10 and the patch 11.

Referring again to FIGS. 1-4, each locking assembly 25 comprises an anchor block 26, a locking strap 27, and a buckle 28. The anchor block 26 is secured to the base 10, and the anchor block 26 has a length disposed substantially parallel to the longitudinal axis 17 of the base 10. The anchor block 26 has a first side 29, a second side 30, the first side 29 and second side 30 being separated by a crown 31. The first side 29 of the anchor block 26 has a recess 32 for receiving the locking strap 27, as described below. In one embodiment, the anchor block 26 is attached to the base 10 at a location offset in the transverse direction 2b from the longitudinal axis 17. In this configuration, the anchor block 26 is attached to the table 15 and to the apron 16 on one side of the longitudinal axis 17. However, in this configuration the anchor block 26 does not attach to the apron 16 on both sides of the longitudinal axis 17.

Each locking strap 27 comprises a root 33, a spine 34, a tip 35, and a plurality of locking members 36, such as or fins, tabs, or the like. Each of the fins 36 has a trailing edge 37 and a leading edge 38. The trailing edge 37 is disposed at an orientation that is about perpendicular to the spine 34 when the gripping device 1 is in its undeformed shape. The leading edge 38 is disposed at an angle of about 40° in relation to the trailing edge 37 (see FIG. 10). The fins 36 are disposed in pairs symmetrically about the spine 34. The pairs of fins 36 are spaced at intervals along the spine 34 such that the space between the pairs of fins 36 defines a notch 39.

The root 33 of the locking strap 27 is anchored in, or attached within, the recess 32 of the first side 29 of the anchor block 26. The root 33 comprises an elbow 21 having a cutout groove 22 on the inside of the elbow 21 to promote flexibility. The elbow 21 of the root 33 biases the orientation of the locking strap 27 such that in its undeformed shape, the locking strap 27 is oriented in a plane that is substantially parallel to the plane of the table 15 of the base 10. At least a portion of the first side 29 of the anchor block 26 is curved toward the crown 31, which is the direction opposite that of the curvature of the outside of the elbow 21. Thus, the interface between the elbow 21 and the first side 29 defines a creased groove 23.

Figure 4:
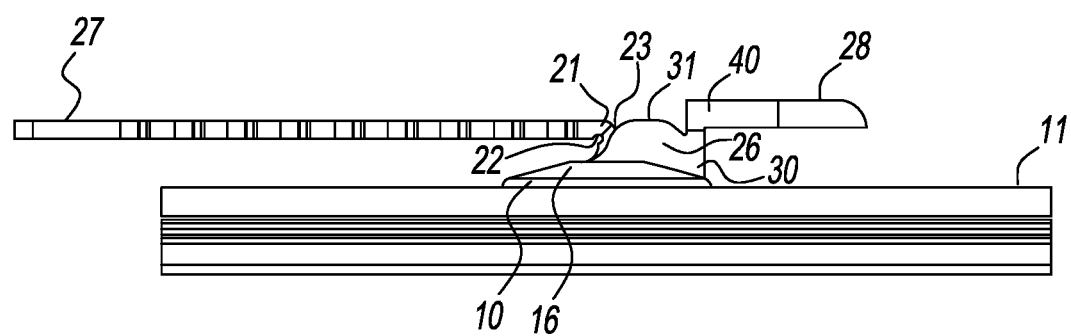
FIG. 4 is a side view of one embodiment of a gripping device.

FIG. 4 illustrates an angle located at the creased groove 23 in which a small French size tubing member 5 may be placed, as described above. The angle of the creased groove 23 is preferably about 80°. This angle minimizes or eliminates the possible mechanical occluding of tubing members 5 enclosed by the gripping device 1 post threading of the locking strap 27 into the aperture 43.

Referring again to FIGS. 1-4, each buckle 28 comprises a root 40 and a distal end 41. The root 40 is attached to the second side 30 of the anchor block 26. The root 40 comprises a Y-shaped or a U-shaped structure, such as a yoke 42. The open end of the yoke 42 is placed against the second side 30 of the anchor block 26 such that an aperture 43 is defined by the second side 30 and the yoke 42. The width of the aperture 43 is slightly larger than the width of the spine 34 of the locking strap 27, but smaller than the tip to tip width of a pair of fins 36. In one embodiment, the tip to tip width of the fins is about 2 mm larger than the width of the aperture 43. The buckle 28 has a thickness sized to snugly seat in a notch 39 between pairs of fins 36. In another embodiment, the aperture 43 is disposed within the buckle 28, and the second side 30 does not form a part of the aperture 43.

Figure 7:
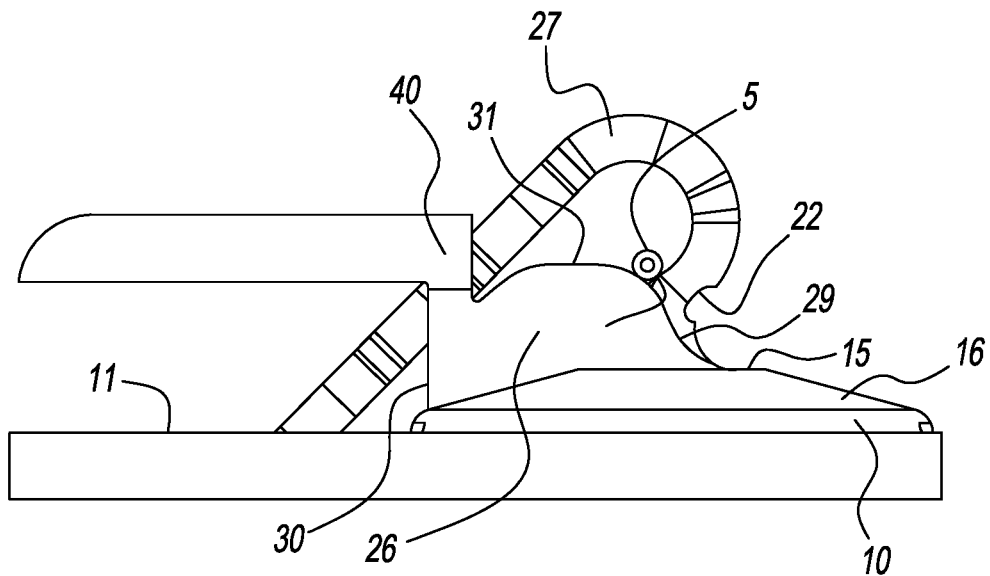
FIG. 7 is a side view of one embodiment of a gripping device, showing a locking strap inserted through the aperture of the buckle.
Figure 8:
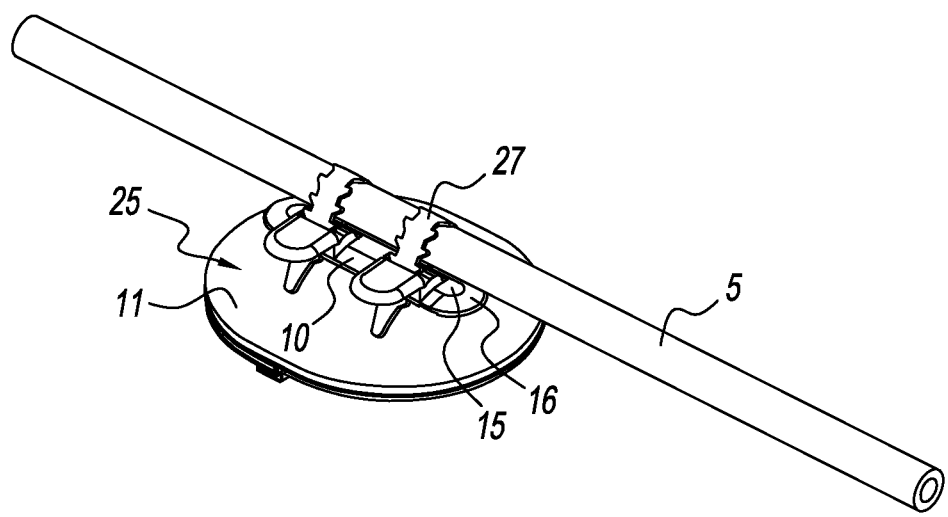
FIG. 8 is a perspective view showing a tubing member securely retained by one embodiment of a gripping device.

Referring to FIGS. 7-8, the gripping device 1 is capable of releasably securing tubing members 5 of various sizes. For a large diameter tubing member 5, one of a relatively large French size, the tubing member 5 is first placed in the creased groove 23 between the first side 29 of the anchor block 26 and the root 33 of the locking strap 27 attached to the anchor block 26. The locking strap 27 is then looped over the tubing member 5, and the tip 35 of the locking strap 27 is inserted through the aperture 43 of the buckle 28. The tip 35 is then pulled such that the locking strap 27 continues to pass through the aperture 43, thereby forcing one or more pairs of fins 36 through the aperture 43. As the fins 36 pass through the aperture 43, the fins 36 deform in shape, bending toward the trailing edge 37 to enable passage of the relatively wide fins 36 through the relatively narrow aperture 43. The angled orientation of the leading edge 38 of the fins 36 promotes passage of the pairs of fins 36 through the aperture 43. Optionally, the throat 44 of the aperture 43 can comprise angled walls 45 to further promote passage of the fins 36. The orientation of the angled walls 45 can approximate that of the leading edges 38, thus oriented at about 40° with respect to the trailing edges 37.

The locking strap 27 is pulled through the aperture 43 until the locking strap 27 snugly wraps around the tubing member 5, thereby seating the tubing member 5 firmly into the creased groove 23. The locking strap 27 is thus held in place, securing the tubing member 5, because the trailing edge 37 of the fins 36 abut against the root 40 of the buckle 28 in proximity to the aperture 43. In other words, due to the configuration of the fins 36, the retraction force needed to retract the locking strap 27 from the aperture 43 is larger than the insertion force required to insert the locking strap 27 into and through the aperture 43.

For tubing members 5 of a smaller diameter, or smaller French size, such tubing members 5 are secured in a manner similar to that described above. In fact, tubing members 5 of any French size can be seated in the creased groove 23 to minimize mechanical occluding of the fully secured tubing member 5. In an alternative orientation, the tubing members 5 can be placed on the crown 31 rather than seated in the creased groove 23. However, this orientation may increase the risk of mechanical occluding of the tubing member 5.

In one embodiment, the gripping device 1 is made from an amorphous thermoplastic elastomer polymer, herein referred to as "TPE," which is extremely elastic (reaching 870% elongation) with a very high tear strength value (19.3 kN/m). TPE materials exhibit the properties of both plastics and rubbers. Additionally the natural tribological or frictional nature of the TPE allows for superior gripping to other polymeric materials, which is a characteristic not present in prior art gripping devices. The designed surface area of the interfacing surface of the present gripping device 1 establishes a large tangential contact area to the polymer tubing members 5.

Thermoplastic elastomers are generally low modulus, flexible materials that exhibit substantial elastic deformation. These materials may be subjected to temporary shape changes that are normally self-reversing after a force is removed, thus enabling an object made from this material to return to its original shape. Elastic deformation is a change in the shape of a material at low stress, and this deformation is recoverable after the stress is removed. This type of deformation involves stretching of the bonds of the TPE material, but the atoms do not slip past each other.

The tribological aspect of the material chosen for the gripping device 1 can be defined as the contact behavior of the interface, in that it depends not only on the morphology of solids, but the elasticity, viscoelasticity, and surface hardness of the contact surfaces of the polymers that will come in contact with the surface of the gripping device 1. The unique design features of the gripping device, coupled with the tribological aspects of the TPE, increase the run-in friction of the interface of the gripping device 1 and the tubing members 5. Run-in friction is an unsteady state friction. It refers to a friction state where the frictional coefficient varies as the sliding time (sliding distance) during the beginnings of relative motion. For example, if a polymeric sphere slides across a relatively clean, smooth, and hard surface, the majority of resulting frictional forces arise from the interfacial adhesion. Therefore if polymeric surfaces slide over relatively clean, smooth, hard surfaces, such as normally stiff PVC tubing used for LVAD drivelines, most frictional forces are resulted from the interfacial adhesion created by the contacting surfaces.

The effect of this phenomenon is that the use of this TPE material with these polymeric characteristics increases the mutual attraction of the polymeric substances used in the construction of flexible polymer tubing and polymer coated cables. This increases the coefficient of friction between the contacting polymeric surfaces of the tubing members 5 and the gripping device 1, thus minimizing or eliminating chance occurrence of the tubing members 5 slipping or sliding relative to the gripping device 1. The mechanical design features of the gripping device 1 coupled with this TPE material allow for maximum surface contact between the gripping device 1 and the tubing members 5.

Figure 2:
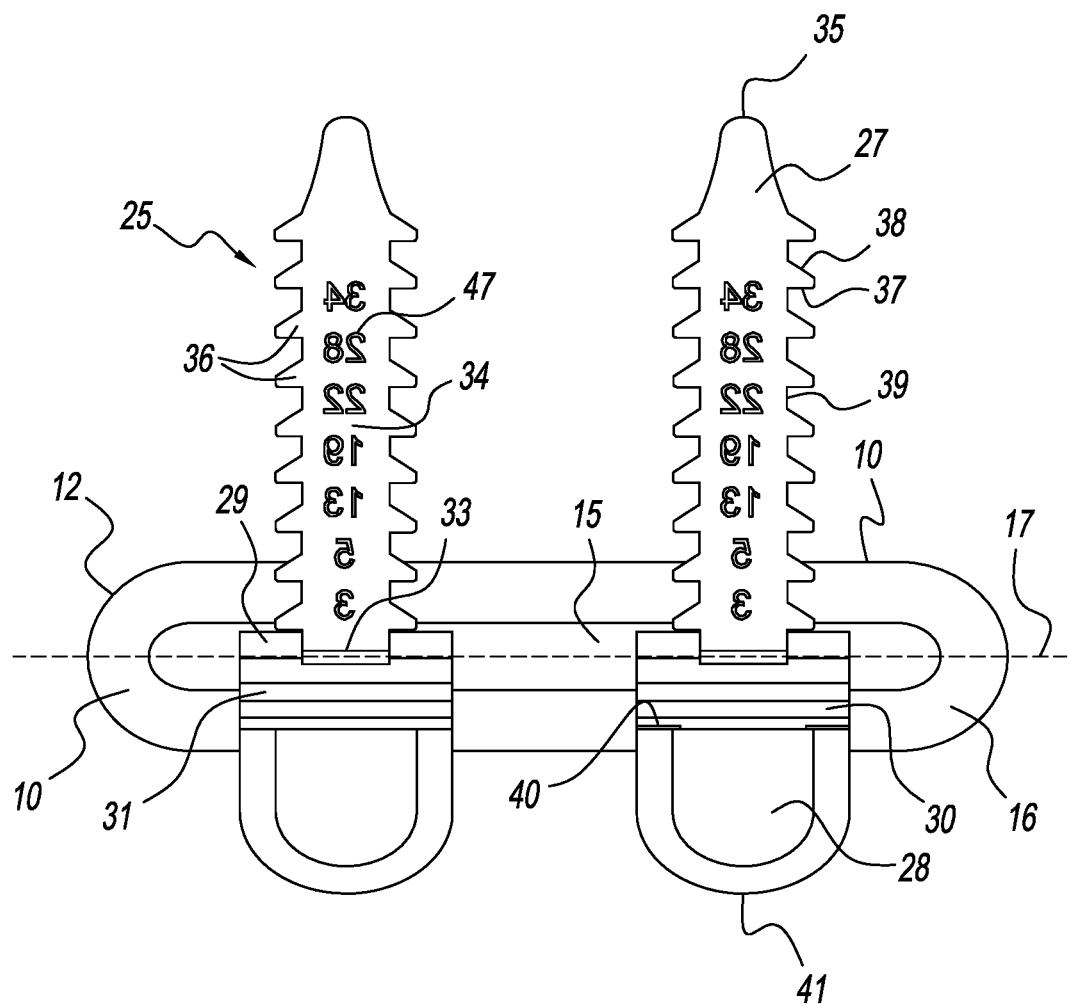
FIG. 2 is a top view of one embodiment of a gripping device in its undeformed shape.
Figure 3:
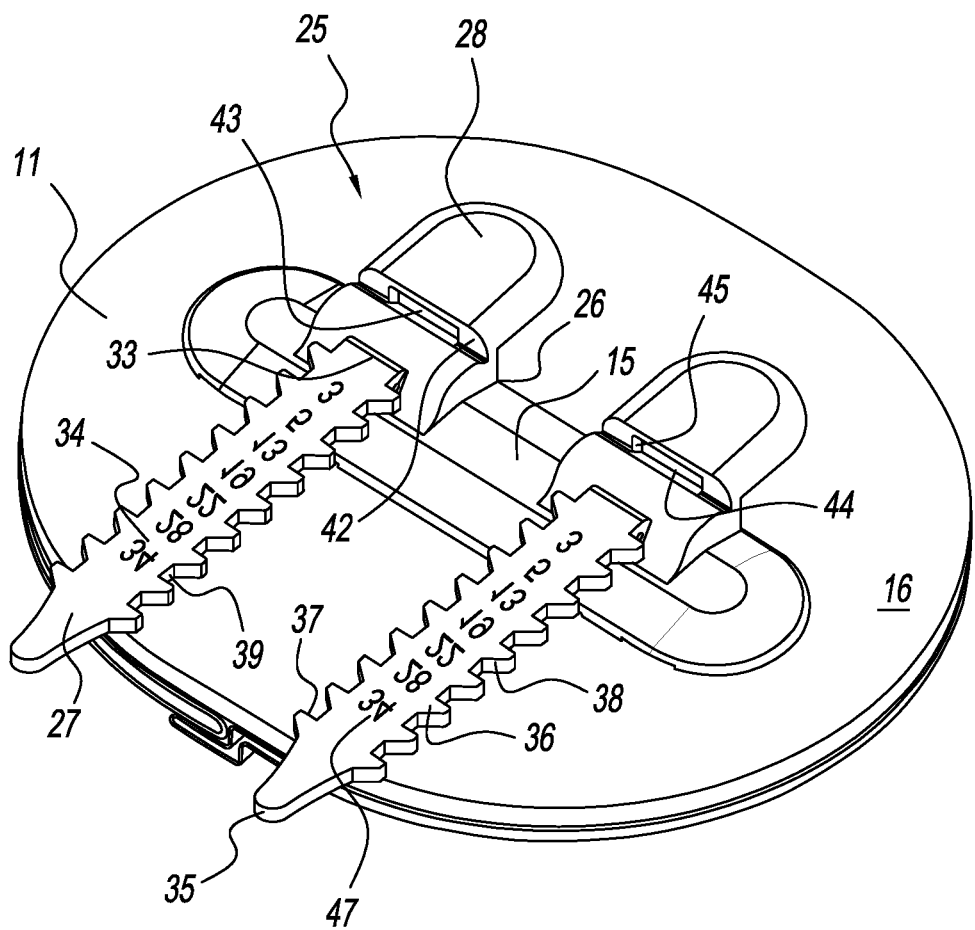
FIG. 3 is an isometric view of one embodiment of a gripping device in its undeformed shape.

In one exemplary embodiment, shown in FIGS. 1-3, a multi-strap design has two or more locking assemblies 25 that are flexible, extremely elastic (about 870% elongation), and attached to the base 10 adjacent to each other. These locking assemblies 25 may be molded onto the base 10 or attached by an adhesive or other suitable attachment material. The locking straps 27 of each locking assembly 25 can be manufactured in various lengths that can accommodate very small (3. Fr) to very large (47. Fr) sized tubing members 5.

Figure 9:
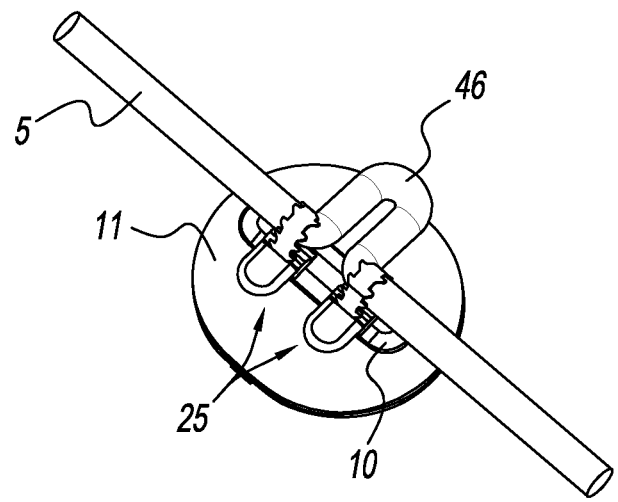
FIG. 9 is a perspective view showing a tubing member having a service loop securely retained by one embodiment of a gripping device.

In one embodiment, shown in FIG. 9, the distance between the adjacent locking assemblies 25, as measured along the length of the base 10, is calculated to allow for a service loop 46 in the tubing member 5. The distance should be large enough such that the service loop 46 does not kink or otherwise mechanically occlude the tubing member 5. In many types of tubing members 5, approximately 30 mm length service loops 46 may be desirable.

Figure 10:
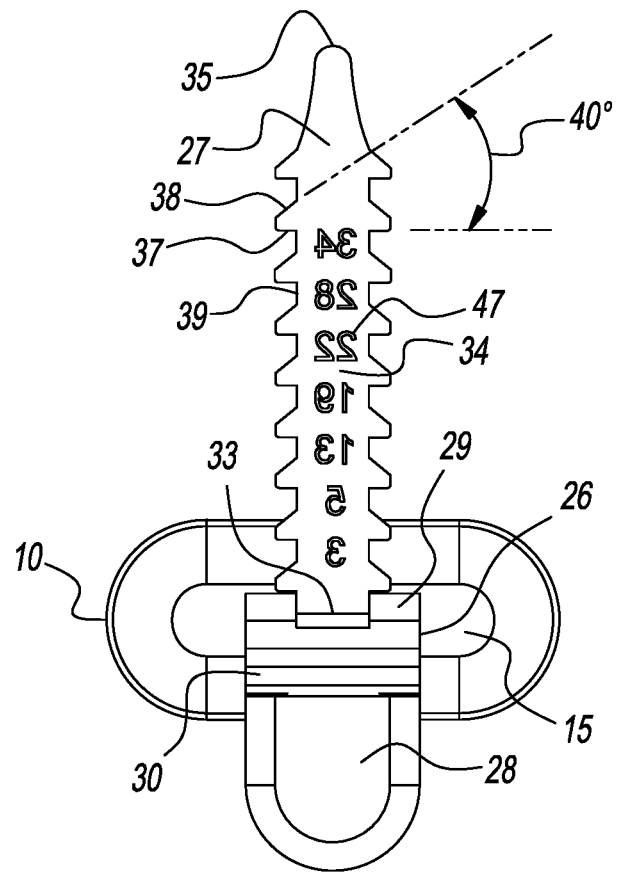
FIG. 10 is a top view of one embodiment of a gripping device.

In another embodiment of the gripping device 1, shown in FIG. 10, the gripping device 1 has a single locking assembly 25, which is located at about the midpoint along the length of the base 10.

In another embodiment of the locking assembly 25, shown in FIGS. 1-3, and 10, each of the locking straps 27 further comprises a visual indicator 47 corresponding to the approximate diameter of tubing member 5 to be secured. For example, the visual indicator 47 could be a series of numerical references to approximate French size of the tubing member 5 to be secured. The locking straps 27 are threaded into the aperture 43 of the buckle 28, as described above. The locking straps 27 are inserted through the buckle 43 to an extent corresponding to the visual indicator's 47 designation of the French size of the tubing member 5. Use of this type of visual indicator 47 ensures that each tubing member 5 is securely retained by the gripping device 1 without unnecessary over tightening, which can cause mechanical occlusion of the tubing member 5.

In one embodiment, the height of the base is about 2 mm. In this embodiment, the overall height of the undeformed gripping device 1 is about 7.5 mm.

The low profile of the base 10 enables other dimensions of the gripping device 1 to be fabricated in a manner such that there is little or no loss in the mechanical strength or elastic properties of the gripping device 1. The low profile of the gripping device 1 is beneficial to minimize or eliminate the tubing member 5 from snagging, catching, entangling, or otherwise interfering with other patient monitoring or therapeutic devices or lines.

The foregoing embodiments are merely representative of the gripping device and not meant for limitation of the invention. For example, persons skilled in the art would readily appreciate that there are several embodiments and configurations of locking assembly features and other components will not substantially alter the nature of the gripping device. Likewise, elements and features of the disclosed embodiments could be substituted or interchanged with elements and features of other embodiments, as will be appreciated by an ordinary practitioner. Consequently, it is understood that equivalents and substitutions for certain elements and components set forth above are part of the gripping device described herein, and the true scope of the invention is set forth in the claims below.

What is claimed is:

1. A gripping device for securing a flexible polymer tubing member to the skin of a medical patient, the gripping device comprising:
    an elongated base having a top and a longitudinal axis, the top having a sloped apron surrounding a central table;
    one or more locking assemblies, each locking assembly comprising:
        an anchor block attached to the base at an offset orientation in a transverse direction in relation to the longitudinal axis of the base such that the anchor block is attached to the table and to the apron without being attached to the apron on both sides of the longitudinal axis, the anchor block having a first side and a second side separated by a single crown;
        a locking strap having a root and a plurality of fins, the root anchored to the first side of the anchor block such that a creased groove is defined by an interface between the first side and the locking strap;
        the creased groove disposed adjacent to the crown and above the table in substantial vertical alignment with the longitudinal axis of the base, the crease groove disposed such that the root and the first side of the anchor block contact the polymer tubing member when the polymer tubing member is seated in the creased groove; and
        a buckle having a root and a distal end, the root attached to the second side of the anchor block, and the root having a yoke such that an aperture is defined by the second side of the anchor block and the yoke.

2. The gripping device of claim 1, wherein the locking strap has an open position and a closed position, the locking strap further comprising a visual indicator having a series of numerical references disposed on the locking strap, the visual indicator corresponding to a diameter of a tubing member, wherein when the locking strap is in the open position the numerical references appear reversed with respect to the appearance of the numerical references on the closed position of the locking strap.

3. The gripping device of claim 2, wherein the base further comprises a bottom having an interface member that comprises a plurality of cleats disposed in a dovetail orientation.

4. The gripping device of claim 2, wherein the base further comprises a bottom having an interface member that comprises an irregular surface feature.

5. The gripping device of claim 2, wherein the root of each of the locking straps further comprises an elbow having an outside and an inside, the outside curving away from the base, and the inside having a cutout groove.

6. The gripping device of claim 5, wherein the locking strap further comprises a spine with the fins disposed in pairs symmetrically about the spine, the pairs of fins disposed such that a notch is defined between adjacent fin pairs, and the buckles have a thickness sized to snugly seat in the notch.

7. The gripping device of claim 6, wherein the interface member comprises a plurality of cleats disposed in a dovetail orientation.

8. The gripping device of claim 6, wherein the interface member comprises an irregular surface feature.

9. The gripping device of claim 1, wherein the root of the locking strap further comprises an elbow such that in an undeformed shape of the locking strap, the elbow biases the orientation of the locking strap into a plane that is substantially parallel to the plane of the table of the base, the interface that defines the creased groove further comprising the elbow.

10. A gripping device for securing a flexible polymer tubing member to the skin of a medical patient, the gripping device comprising:
    an elongated base having a top and a longitudinal axis, the top having a sloped apron surrounding a central table;
    an adhesive patch connected to the base by an adhesive disposed between the interface member and the adhesive patch;
    two locking assemblies attached to the base, each locking assembly comprising:
        an anchor block attached to the base at an offset orientation in relation to the longitudinal axis of the base such that the anchor block is attached to the table and to the apron without being attached to the apron on both sides of the longitudinal axis, the anchor block having a first side and a second side separated by a single crown;
        a locking strap having a root and a plurality of fins, the root anchored to the first side of the anchor block such that a creased groove is defined by an interface between the first side and the locking strap, the creased groove disposed adjacent to the crown and above the table; and
        a buckle having a root and a distal end, the root attached to the second side of the anchor block, and the root having a yoke such that an aperture is defined by the second side of the anchor block and the yoke;
    each locking assembly having an open position and a closed position, wherein:
        the open position comprises the locking strap disengaged from the aperture, and
        the closed position comprises the locking strap inserted through the aperture such that the fins engage the buckle and the locking strap is retained in contact with the yoke and in contact with the second side of the anchor block, the locking strap configured for seating the polymer tubing member in the creased groove such that the polymer tubing member is retained in contact with the first side of the anchor block and in contact with the root of the locking strap; and the locking assemblies disposed such that the creased grooves are oriented in alignment with each other and placed at an orientation substantially parallel to the longitudinal axis of the base.

11. The gripping device of claim 10, wherein each locking strap further comprises a visual indicator having a series of numerical references disposed on the locking strap, the visual indicator corresponding to a diameter of a tubing member, wherein when the locking assembly is in the open position the numerical references appear reversed with respect to the appearance of the numerical references on the closed position of the locking assembly.

12. The gripping device of claim 11, wherein the base further comprises a bottom having an interface member that comprises a plurality of cleats disposed in a dovetail orientation.

13. The gripping device of claim 11, wherein the base further comprises a bottom having an interface member that comprises an irregular surface feature.

14. The gripping device of claim 11, wherein the root of each of the locking straps further comprises an elbow having an outside and an inside, the outside curving away from the base, and the inside having a cutout groove.

15. The gripping device of claim 14, wherein the locking strap further comprises a spine with the fins disposed in pairs symmetrically about the spine, the pairs of fins disposed such that a notch is defined between adjacent fin pairs, and each of the buckles has a thickness sized to snugly seat in the notches on the mating locking strap.

16. The gripping device of claim 15, wherein the interface member comprises a plurality of cleats disposed in a dovetail orientation.

17. The gripping device of claim 10, wherein the root of the locking strap further comprises an elbow such that in an undeformed shape of the locking strap, the elbow biases the orientation of the locking strap into a plane that is substantially parallel to the plane of the table of the base, the interface that defines the creased groove further comprising the elbow.

18. A gripping device for securing a flexible polymer tubing member to the skin of a medical patient, the gripping device comprising:

an elongated base having a top and a longitudinal axis, the top having a sloped apron surrounding a central table;

one or more locking assemblies attached to the base, each locking assembly comprising:

an anchor block attached to the base at an offset orientation in a transverse direction in relation to the longitudinal axis of the base such that the anchor block is attached to the table and to the apron without being attached to the apron on both sides of the longitudinal axis, the anchor block having a first side and a second side separated by a single crown;

a locking strap having a root and a plurality of fins, the root anchored to the first side of the anchor block;

a seat for seating the polymer tubing member, the seat comprising an interface between the first side of the anchor block and the root of the locking strap, the seat disposed adjacent to the crown and above the table such that the root and the first side of the anchor block contact the polymer tubing member when the polymer tubing member is seated in the seat; and a buckle having a root and a distal end, the root attached to the second side of the anchor block, and the root having a yoke such that an aperture is defined by the second side of the anchor block and the yoke;

each locking assembly having an open position and a closed position, wherein:

the open position comprises the locking strap disengaged from the aperture, and the closed position comprises the locking strap inserted through the aperture such that the fins engage the buckle and the locking strap is retained in contact with the yoke and in contact with the second side of the anchor block, the locking strap configured for seating the polymer tubing member in the seat such that the polymer tubing member is retained in contact with the first side of the anchor block and in contact with the root of the locking strap.

19. The gripping device of claim 18, further comprising an adhesive patch connected to the base by an adhesive disposed between the interface member and the adhesive patch.

20. The gripping device of claim 18, wherein the root of the locking strap further comprises an elbow such that in an undeformed shape of the locking strap, the elbow biases the orientation of the locking strap into a plane that is substantially parallel to the plane of the table of the base, the interface that defines the creased groove further comprising the elbow.

* * * * *